(12) United States Patent
Deshpande et al.

(10) Patent No.: US 11,382,879 B2
(45) Date of Patent: Jul. 12, 2022

(54) METHODS FOR IMPROVING PHYSICAL PERFORMANCE AND CAPSICUM COMPOSITIONS USED THEREIN

(71) Applicant: OmniActive Health Technologies Limited, Mumbai (IN)

(72) Inventors: Jayant Deshpande, Charlottetown (CA); Khadija Ghanam, Charlottetown (CA); Vijaya Juturu, Morristown, NJ (US)

(73) Assignee: OmniActive Health Technologies Limited, Mumbai (IN)

( * ) Notice: Subject to any disclaimer, the term of this patent is extended or adjusted under 35 U.S.C. 154(b) by 0 days.

(21) Appl. No.: 16/329,479

(22) PCT Filed: Aug. 29, 2017

(86) PCT No.: PCT/IB2017/055183
§ 371 (c)(1),
(2) Date: Feb. 28, 2019

(87) PCT Pub. No.: WO2018/042330
PCT Pub. Date: Mar. 8, 2018

(65) Prior Publication Data
US 2019/0192453 A1    Jun. 27, 2019

(30) Foreign Application Priority Data
Aug. 30, 2016    (IN) .............................. 201621029468

(51) Int. Cl.
*A61K 31/165*    (2006.01)
*A61K 36/81*    (2006.01)

(52) U.S. Cl.
CPC ............ *A61K 31/165* (2013.01); *A61K 36/81* (2013.01)

(58) Field of Classification Search
None
See application file for complete search history.

(56) References Cited

U.S. PATENT DOCUMENTS

| | | | |
|---|---|---|---|
| 4,592,912 A | 6/1986 | Nickolaus | |
| 2012/0027693 A1 | 2/2012 | Bean et al. | |
| 2014/0343156 A1 | 11/2014 | Bean et al. | |
| 2015/0297546 A1 | 10/2015 | Morita et al. | |
| 2016/0213673 A1 | 7/2016 | Bartos et al. | |

FOREIGN PATENT DOCUMENTS

WO    2006/060505    6/2006

OTHER PUBLICATIONS

Othman et al., Molecules, 2011, vol. 16, No. 10, pp. 8919-8929 (Year: 2011).*
Arciero et al., "Performance Enhancing Diets and the PRISE Protocol to Optimize Athletic Performance", J. Nutrition and Metabolism, vol. 2015, Article ID 715859 (Year: 2015).*
Condor, "One Hot Theory for Athletes", South Florida Sun Sentinel, Jul. 3, 1997 (Year: 1997).*
Oh et al. "Dose-dependent effect of capsaicin on endurance capacity in rats," British Journal of Nutrition (2003), 90, 515-520; (Year: 2003).*
Luo et al. "TRPV1 activation improves exercise endurance and energy metabolism through PGC-1α upregulation in mice," Cell Research (2012) 22:551-564; (Year: 2012).*
Luo et al., "TRPV1 activation improves exercise endurance and energy metabolism through PGC-1α upregulation in mice", Cell Research, vol. 22, No. 3, Jan. 1, 2012, pp. 551-564.
Harada et al.,"AT1 receptor blockers increase insulin-like growth factor-l production by stimulating sensory neurons in spontaneously hypertensive rats", Translational Research, vol. 154, No. 3, Sep. 2009, pp. 142-152.
Herbold et al., "Traditional and Nontraditional Supplement Use By Collegiate Female Varsity Athletes", International Journal of Sport Nutrition and Exercise Metabolism, vol. 14, 2004, pp. 586-593.
Oh et al., "Capsaicin Increases Endurance Capacity and Spares Tissue Glycogen through Lipolytic Function in Swimming Rats", J Nutr Sci Vitaminol, vol. 49, 2003, pp. 107-111.
Haramizu et al., "Capsiate, a Nonpungent Capsaicin Analog, Increases Endurance Swimming Capacity of Mice by Stimulation of Vanilloid Receptors", Biosci. Biotechnol. Biochem., vol. 70, No. 4, 2006, pp. 774-781.
International Search Report, issued in the corresponding PCT application No. PCT/IB2017/055183, dated Oct. 23, 2017, 4 pages.

* cited by examiner

*Primary Examiner* — Jeffrey S Lundgren
*Assistant Examiner* — Michael J Schmitt
(74) *Attorney, Agent, or Firm* — Hamre, Schumann, Mueller & Larson, P.C.

(57) ABSTRACT

Methods of improving physical performance and endurance include administering a *capsicum* composition to a subject. More particularly the methods include administration of an effective amount of a *capsicum* composition including capsaicinoids alone and/or in combination with other nutrients for improvement in performance of physical activities. The methods described include administration of a *capsicum* composition to a subject undergoing physical activity to deliver daily dose of capsaicinoids in an effective amount. The methods include administering a *capsicum* composition to a subject in an effective amount to reduce blood lipids and oxidative stress. Methods for enhancing physical endurance and exhaustion time include administering an effective amount of a *capsicum* composition to a physically active subject, wherein body antioxidants are increased and muscle lactates are decreased, resulting in recovery from muscle fatigue arising due to such indoor and/or outdoor physical activities.

6 Claims, 4 Drawing Sheets

Values less than 0.5 indicate down regulation
Values greater than 2.0 indicate up regulation Values on X axis indicate – doses in microgram/ml
Values on Y axis indicate- relative expression

METHODS FOR IMPROVING PHYSICAL PERFORMANCE AND CAPSICUM COMPOSITIONS USED THEREIN

FIELD

A method for improving physical performance and endurance includes administering a *capsicum* composition to a subject. More particularly, the method includes administering an effective amount of *capsicum* composition alone and or in combination with other nutrients for improvement in performance of physical activities such as exercise, improvement in endurance, fatigue suppression, and post-exercise recovery from muscle fatigue and/or muscle soreness. The composition as described herein is comprised of *capsicum* extract as such or formulated in form of an extended and sustained release stable, free flowing, solid beadlet or powder composition formulated using pharmaceutically and/or nutraceutically acceptable excipient. A method described herein includes administering a *capsicum* composition to a subject undergoing physical activity, as a daily dose of capsaicinoids in an effective amount. The method further includes administering a *capsicum* composition alone or in combination with other nutrients, muscle enhancers, stimulants, essential amino acids, and/or anabolic ingredients for improving physical performance and endurance during activities such as exercise, sports, and other strenuous indoor or outdoor physical activities. The method includes administering a *capsicum* composition to a subject in an effective amount to reduce blood lipids and oxidative stress. The invention also relates to a method for enhancing physical endurance and exhaustion time, by administering an effective amount of a *capsicum* composition to a physically active subject, wherein body antioxidants are increased and muscle lactates are decreased, thus resulting in recovery from muscle fatigue arising due to such indoor and/or outdoor physical activities.

BACKGROUND

Indoor and outdoor physical activities such as sports and exercise are main foundations of health and well-being. Exercise can stimulate vitality, strength, and natural healing mechanisms of body. This stimulation also confers stamina required for carrying out strenuous physical activities from routine life, such as for example fast walking, staircase climbing, prolonged vehicle or machine operation, such as for example driving a car for several hours (e.g. 7 to 8 hours) and/or driving along varying terrain and roads, which may lead to tiredness, or weight lifting. Physical fitness and stamina can be enhanced through indoor and outdoor exercise activities such as for example swimming, cycling, walking, skipping, trekking and so on, or by going to a gym regularly for work-outs. People realize the importance of regular exercise activity. However, on one hand, expenditure on sporting events and sporting products is increasing; and on the other hand, rates of obesity and metabolic diseases has been steadily increasing for decades. Sport activities may be pursued more for focusing on developing talent, rather than focusing on health-care. This cultural message seems to give the wrong impression to our youth—who either excel in sports or may quit physical activity altogether.

Stress of athletic performance is so high that there is continual need to perform better to win and enhance endurance for success. This may give rise to use of performance enhancing drugs. Many professional athletes are reported to use even banned drugs, which is illegal and also comes with side effects. Thus it becomes important to look for safer options, such as natural products or nutraceuticals for improving performance and endurance of the sports person.

Plants which provide us most nutrients and phytochemicals having nutritional or medicinal value are becoming popular for this purpose. From an athlete's perspective, the vitamin and mineral content of fruits and vegetables has an important role in maintaining health and well-being and optimizing exercise performance during periods of heavy training. These vitamins and minerals also have a functional role in recovery following strenuous exercise. These nutrients cannot be synthesized by the body, so athletes consume a diet rich in desired nutrients to support daily training and recovery from training.

Herbal dietary supplements are used to a large extent to fulfill this purpose. Herbold N H, Visconti B K, Frates S, Bandini L, Int J Sport Nutr Exerc Metab. 2004 October; 14(5):586-93] reported that 17 percent of female collegiate athletes used herbal/botanical supplements. Herbal dietary supplements are marketed to physically active individuals for a variety of reasons, including increasing energy, inducing weight loss, promoting muscle growth, or inducing other physiological or metabolic responses that may enhance exercise performance. Some other dietary supplements are used to increase mental alertness, stimulate fat-burning metabolism, and help enhance physical performance. Some sports drinks and sports bars contain herbals as well.

The increasing number and availability of sports supplements presents an ongoing challenge for the practitioner and the athlete to keep up-to-date about the validity of the claims and scientific evidence. Although use of nutritional products that enhance performance is highly prevalent, the fact remains that very few improve performance and some may cause concern because of false claims. Hence it is important to know the right choices of nutritional supplements that help improve performance with minimum side effects and also help to improve endurance.

Although herbal sources such as Aswagandha, curcumin, *ginseng*, gingko, *Echinacea*, *Rhodiola* are being used and evaluated for improving exercise and sports performance, there is a need for compositions which also improve endurance and exhaustion time for these activities for sustained performance. Research is also ongoing on *capsicum* which is mainly reported for its weight management effect. *Capsicum* is a pepper that contains active capsaicinoids, which has property of warming and improving circulation to all parts of body, thus easing joint pain of arthritis, muscle spasms, and cluster headaches. It is included in many cuisines and is a great aid for digestion and is believed to regulate heart and blood pressure and even improve athletic performance. There are some references which relate to the use of *capsicum* for improving performance in physical activities like swimming in animal models.

PCT patent application WO2006060505 relates to compositions comprising a combination of one or more vanilloid receptor agonists like capsaicin and methylxanthine compound in a nutritional supplement. The disclosed compositions are synergistically effective to enhance cognitive performance and boost energy, increase alertness, mental concentration, mental focus, and wakefulness.

U.S. Pat. No. 4,592,912 relates to a topical dosage form containing aqueous extract of *capsicum* from *Capsicum frutescens* along with slippery elm and myrrh gum for treatment of muscular aches and pains. The composition is applied topically to an individual's body in a thin layer form for the relief of or for the prevention of muscular aches, pains, cramps, and muscular spasms.

US20140343156 relates to a method for treatment or prevention of muscle cramp resulting from exercise, nocturnal cramp or menstrual cramp by orally administering to the subject solid or liquid capsaicin formulation comprising of at least one excipient.

Oh T W et al. (J Nutr Sci Vitaminol (Tokyo). 2003 April; 49(2):107-11) describe the influences of various doses of capsaicin on endurance capacity in rat models. The experiments were carried out by attaching weights to rat tails and they were allowed to swim for a specific time period to check endurance, after administering different doses of capsaicin before starting swimming activity. It was observed that swimming endurance was improved with higher capsaicin dose which might be induced through the sparing of muscle glycogen and the rise of non-esterified fatty acids following the increase of circulating catecholamine.

Haramizu S et al. (Biosci. Biotechnol. Biochem. 70 (4), 774-781, 2006) describe the effect of capsiate on swimming capacity of mice in an adjustable-current water pool. The results suggest that the oral administration of capsiate enhanced fat oxidation and spared carbohydrate utilization, and consequently increased endurance swimming capacity of the mice via stimulation of their vanilloid receptors.

US 20150297546 relates to a method of promoting blood flow, comprising a step of administering citrulline or a salt thereof and capsaicin or capsaicinoids for improvement of athletic performance exhibited in relation to peripheral vasodilatation, suppression of fat accumulation, improvement of skin quality, or prophylaxis of ischemic disease.

US20160213673 describes a method of enhancing the endurance of a mammal comprising administering a composition comprising dihydrocapsiate, caffeine and arginine to enhance the endurance of said mammal, said enhanced endurance being measured by a decrease in the rating of perceived exertion (RPE) during physical exertion, such as during running, swimming, weight lifting and/or walking, as compared to the RPE of said mammal prior to being administered the composition.

SUMMARY

The references report about evaluation of capsaicin in experimental animals at various doses to study their effect on enhanced physical activities, cognitive performance or for treatment of ailments such as muscle cramps. The references describe the effect of capsaicin on central nervous system hormones or receptors. The reported studies generally employ a swim test model which is used as a behavior test.

In an embodiment, a *capsicum* formulation or composition is administered to exercising subjects and an evaluation thereof shows results in enhanced physical performance, endurance, and also treatment of muscle soreness. It is also observed that the effect of increased physical performance and endurance is significantly enhanced in a subject administered with an effective amount of a *capsicum* composition, while the subject is also undergoing physical activity as compared to the effect observed in a subject not undergoing any physical activity.

By "undergoing physical activity" it is meant as a subject who regularly engages in sports or exercise activity, or physical activity where stamina during a certain period is needed to avoid fatigue during the day.

By "not undergoing physical activity" it is meant as one who is has a sedentary lifestyle, for example, not engaging in regular exercise or sports activity or who may not be walking, jogging, climbing, and/or any other activities for certain amount of time, which would be considered physical activity. For example, one may be leading a normal daily life and doing his/her job, but does not do any additional physical activity, which requires some stamina, or would be considered strenuous, or which needs further energy.

In an embodiment, method is described herein for improving physical performance and endurance, the method includes administering an effective amount of a *capsicum* composition to a subject undergoing physical activity. The *capsicum* composition may be in the form of a *capsicum* extract including capsaicinoids; or the extract may be formulated in the form of solid, free flowing solid dosage form, which is easy to administer. According to the method, when the *capsicum* composition is administered in an effective amount to the subject undergoing exercise activity, improvement in performance as well as endurance is observed. The method also results in improvement in fatigue suppression during endurance exercise and post-exercise recovery from muscle fatigue and/or muscle soreness.

The composition as described herein includes a *capsicum* extract or an extract formulated in the form of an extended and sustained release stable, free flowing, and solid composition using at least one food grade or pharmaceutically acceptable excipient. The excipient may be selected from, but not restricted to hydrophilic carrier, antioxidant, stabilizer, diluent, or the mixture thereof. In an embodiment, the composition includes capsaicinoids and/or non-capsaicinoids.

In an embodiment, a *capsicum* composition may be administered in the form of a *capsicum* extract or an extract formulated as *capsicum* beadlets, in a daily dose so as to provide at or about 0.01 mg/kg body weight to at or about 200 mg/kg body weight of capsaicinoids to the subject. In an embodiment, the composition may be administered in a daily dose to provide at or about 10 mg/kg body weight to at or about 100 mg/kg body weight/of capsaicinoids to the subject for enhanced stamina and exercise endurance.

In an embodiment, a daily dose includes at or about 0.01 mg/kg body weight to at or about 150 mg/kg body weight of capsaicinoids to the subject.

In an embodiment, a daily dose includes at or about 0.01 mg/kg body weight to at or about 100 mg/kg body weight of capsaicinoids to the subject.

In an embodiment, a daily dose includes at or about 0.01 mg/kg body weight to at or about 80 mg/kg body weight of capsaicinoids to the subject.

In an embodiment, a daily dose includes at or about 0.01 mg/kg body weight to at or about 20 mg/kg body weight of capsaicinoids to the subject.

In an embodiment, a daily dose includes at or about 0.01 mg/kg body weight to at or about 10 mg/kg body weight of capsaicinoids to the subject.

In an embodiment, a daily dose includes at or about 0.01 mg/kg body weight to at or about 1 mg/kg body weight of capsaicinoids to the subject.

In an embodiment, a daily dose includes at or about 1 mg/kg body weight to at or about 200 mg/kg body weight of capsaicinoids to the subject.

In an embodiment, a daily dose includes at or about 1 mg/kg body weight to at or about 150 mg/kg body weight of capsaicinoids to the subject.

In an embodiment, a daily dose includes at or about 1 mg/kg body weight to at or about 100 mg/kg body weight of capsaicinoids to the subject.

In an embodiment, a daily dose includes at or about 1 mg/kg body weight to at or about 80 mg/kg body weight of capsaicinoids to the subject.

In an embodiment, a daily dose includes at or about 1 mg/kg body weight to at or about 20 mg/kg body weight of capsaicinoids to the subject.

In an embodiment, a daily dose includes at or about 1 mg/kg body weight to at or about 10 mg/kg body weight of capsaicinoids to the subject.

In an embodiment, a daily dose includes at or about 10 mg/kg body weight to at or about 200 mg/kg body weight of capsaicinoids to the subject.

In an embodiment, a daily dose includes at or about 10 mg/kg body weight to at or about 150 mg/kg body weight of capsaicinoids to the subject.

In an embodiment, a daily dose includes at or about 10 mg/kg body weight to at or about 100 mg/kg body weight of capsaicinoids to the subject.

In an embodiment, a daily dose includes at or about 10 mg/kg body weight to at or about 80 mg/kg body weight of capsaicinoids to the subject.

In an embodiment, a daily dose includes at or about 10 mg/kg body weight to at or about 20 mg/kg body weight of capsaicinoids to the subject.

In an embodiment, a daily dose includes at or about 20 mg/kg body weight to at or about 200 mg/kg body weight of capsaicinoids to the subject.

In an embodiment, a daily dose includes at or about 20 mg/kg body weight to at or about 150 mg/kg body weight of capsaicinoids to the subject.

In an embodiment, a daily dose includes at or about 20 mg/kg body weight to at or about 100 mg/kg body weight of capsaicinoids to the subject.

In an embodiment, a daily dose includes at or about 20 mg/kg body weight to at or about 80 mg/kg body weight of capsaicinoids to the subject.

In an embodiment, a daily dose includes at or about 80 mg/kg body weight to at or about 200 mg/kg body weight of capsaicinoids to the subject.

In an embodiment, a daily dose includes at or about 80 mg/kg body weight to at or about 150 mg/kg body weight of capsaicinoids to the subject.

In an embodiment, a daily dose includes at or about 80 mg/kg body weight to at or about 100 mg/kg body weight of capsaicinoids to the subject.

In an embodiment, a daily dose includes at or about 100 mg/kg body weight to at or about 200 mg/kg body weight of capsaicinoids to the subject.

In an embodiment, a daily dose includes at or about 100 mg/kg body weight to at or about 150 mg/kg body weight of capsaicinoids to the subject.

In an embodiment, a daily dose includes at or about 150 mg/kg body weight to at or about 200 mg/kg body weight of capsaicinoids to the subject.

In an embodiment, the method includes evaluating the effect of a *capsicum* composition through an in-vitro cell line study on various sports nutrition biomarkers such as mitochondrial oxygen consumption, mitochondrial mass, IGF-1, and cortisol. In an embodiment, the method as described herein includes evaluating the effect of *capsicum* composition, by administering an effective amount to a subject undergoing physical activity, as an in-vivo animal model and/or to human volunteers, on various plasma and muscle antioxidants, lipid profile, protein levels and actual effect on time to exhaustion and run time. In an embodiment, the method as described herein includes use of a *capsicum* composition, such as by administering the composition, to enhance exercise performance and endurance through effective utilization of lipids such as cholesterol and triglycerides by increasing phosphorylated adenosine monophosphate (AMP) activated protein kinase (pAMPK) and nuclear erythroid derived factor-like 2 (Nrf2). In an embodiment, a *capsicum* composition as used herein reduces the lactate amount in muscles, enhances running performance, increases heme-oxygenase (HO-1) and decreases interleukin (IL-10) and thus enhances exhaustion time as well as running performance in exercising subjects.

In an embodiment, the composition may be administered to exercising subjects either in the form of a *capsicum* extract or the extract formulated in the form of a free flowing solid formulation prepared, for example, as an extended and sustained release beadlet or powder using nutraceutically or pharmaceutically acceptable excipient(s). In an embodiment the *capsicum* extract is prepared from various varieties of paprika selected from the group of, but not limited to, varieties such as for example Teja and Namdhari. More particularly, the composition herein may be comprised of the *capsicum* extract obtained from varieties of *Capsicum annum* such as Teja and Namdhari.

In an embodiment, the *capsicum* extract as described herein is prepared by an industrially viable process which is comprised of employing non-polar, semi-polar, polar solvents or combinations thereof in suitable ratios. In an embodiment, the composition is prepared by using a combination of polar and non-polar solvents in a suitable ratio for an extraction cycle, followed by purification of the extract by using polar solvent(s) to obtain the extract. In an embodiment, the composition including the extract is safe for human consumption and includes biologically active chemical constituents including capsaicinoids and in some embodiments, further includes non-capsaicinoid compounds.

In an embodiment, the composition may be administered alone or in combination with other nutrients, muscle enhancers, stimulants, essential amino acids, and/or anabolic ingredients for improving exercise performance and endurance during indoor and outdoor physical activities such as exercise, sports, and other physical strenuous activities in normal routine.

In an embodiment, the method described herein includes administering an effective amount of a *capsicum* composition to a subject undergoing physical activity such as exercise, wherein the administering lowers oxidative stress significantly. In an embodiment, a method for enhancing exercise endurance and exhaustion time, including administering an effective amount of a *capsicum* composition to an exercising subject, wherein the antioxidant amount in the subject is increased and the amount of lactate is decreased, thus resulting in recovery from muscle fatigue during exercise and/or post exercise. *Capsicum* compositions herein are safe for oral administration and are prepared using food grade excipients and reagents and employing conventional equipment, thus it has industrial applicability.

In an embodiment, a method includes administering a *capsicum* composition and evaluating the effect of the composition in exercising subjects through in-vitro tests and in-vivo trials to demonstrate use for increasing performance time and enhancing endurance capacity during indoor and outdoor physical activities, such as exercise, sports and other strenuous routine activities.

In an embodiment, the compositions and methods herein include a *capsicum* composition to overcome the exhaustive exercise-induced oxidative stress and muscle injury, and the methods herein include administering the composition to a subject in need thereof. Such subjects include, for example animals, including mammalian subjects, such as for example exercising human subjects.

In an embodiment, a method for improving physical performance and endurance includes administering an effective amount of a *capsicum* composition to an exercising subject, wherein effective utilization of lipids such as cholesterol and triglyceride is carried out by increasing pAMPK and Nrf2.

In an embodiment, a method includes administering a *capsicum* composition, which reduces the lactate amount in muscles, increases heme-oxygenase (HO-1) and decreases interleukin (IL-10), thus enhancing running performance and exhaustion time, to an exercising subject and reducing muscle soreness resulting from prolonged exercise.

In an embodiment, a method includes administering a *capsicum* composition, which enhances the level and activity of muscle building proteins such as IGF-1. The compositions described herein also enhance content of mitochondrial mass and enhance mitochondrial biogenesis, thus resulting in increasing endurance and stamina in exercising subjects.

In an embodiment, a method includes administering a *capsicum* composition in the form of a *capsicum* extract or as an extract formulated in the form of solid free flowing extended and sustained release formulation, such as for example beadlets, tablets, or capsules using at least one nutraceutical and/or pharmaceutically acceptable excipient. The *capsicum* extract includes compounds such as capsaicinoids and is prepared by a solvent extraction method.

In an embodiment, a *capsicum* composition includes a *capsicum* extract prepared for example from various varieties of paprika. In an embodiment, a *capsicum* composition includes chemical constituents including capsaicinoids in combination with non-capsaicinoids.

In an embodiment, a *capsicum* extract for the *capsicum* composition is prepared from various varieties of paprika selected from the group of, but not limited to, varieties such as for example Teja and Namdhari. More particularly, the composition herein may be comprised of the *capsicum* extract obtained from varieties of *Capsicum annum* such as Teja and Namdhari.

In an embodiment, an industrially viable process is provided for preparation of a *capsicum* composition by employing non-polar, semi-polar, polar solvents or combinations thereof in suitable ratios. In an embodiment, a *capsicum* composition is prepared using a combination of polar and non-polar solvents in a suitable ratio for an extraction cycle, followed by purification of the extract by using polar solvent(s) to obtain the extract. The composition including the extract is safe for human consumption and is comprised of biologically active chemical constituents including capsaicinoids and further may be comprised of non-capsaicinoids.

In an embodiment, a *capsicum* composition includes *capsicum* extract alone and/or formulated with at least one more excipient selected from the group of, but not limited to, carrier, diluents, antioxidant, stabilizer, and the mixture thereof to prepare convenient and stable dosage forms.

In an embodiment, a method includes administering a *capsicum* composition, including capsaicinoids in the form of an extract or in the form of the extract formulated into a stable, free flowing, solid composition to provide extended and sustained release of the active ingredient, to an exercising subject in an effective amount.

In an embodiment, a method includes administering an effective amount of a stable, free flowing, solid composition of *capsicum* including capsaicinoids, which is manufactured using extrusion spheronization or beadlet technology.

In an embodiment, a method for improving exercise performance and endurance includes administering a *capsicum* composition in an effective daily dose of at or about 0.01 mg/kg body weight to at or about 200 mg/kg body weight of capsaicinoids to an exercising subject. In an embodiment, the composition is administered as a daily dose of at or about 10 mg/kg body weight to at or about 100 mg/kg body weight of capsaicinoids to the exercising subject.

In an embodiment, a method of improving exercise performance and endurance by reducing oxidative stress and increasing oxidants in a subject includes administering an effective amount of a *capsicum* composition, thus enhancing effect of exercise in subjects.

In an embodiment, a *capsicum* composition herein also enhances endurance of an exercising subject and enhances recovery from muscle fatigue and muscle soreness by decreasing amount of lactate and muscle oxidative stress, and increasing muscle antioxidant. The compositions herein are safe for human administration and are prepared by industrially convenient process and employed in an administration method for enhancing performance and endurance in subjects undergoing physical indoor and outdoor activities.

DETAILED DESCRIPTION

Figure 1:
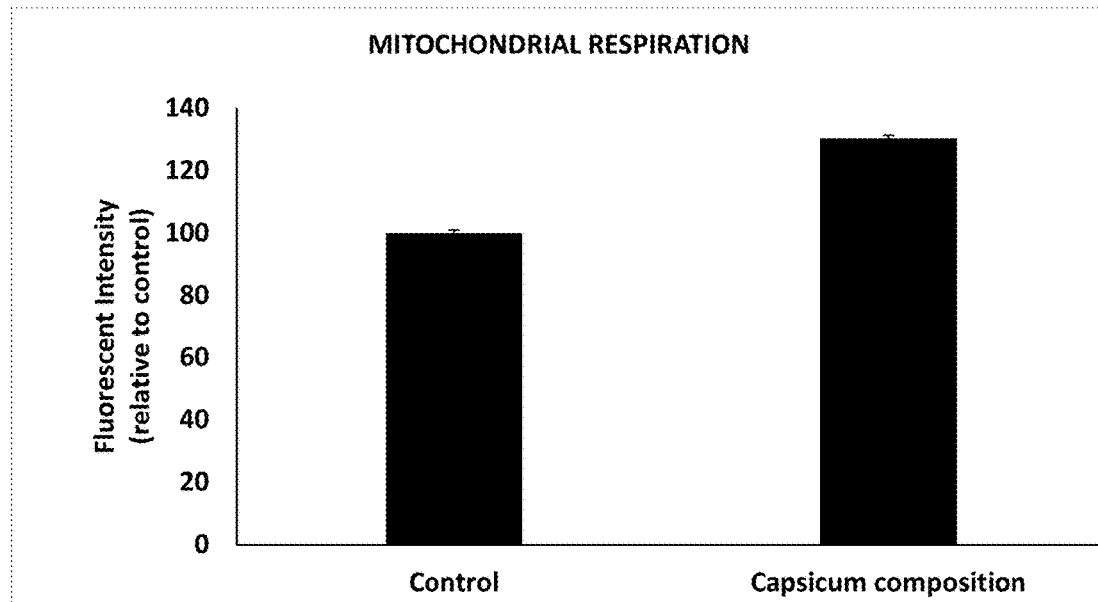
FIG. 1 shows the effect of *capsicum* composition on mitochondrial respiration.

Methods and compositions herein are for improving exercise performance and endurance, such as by administering a *capsicum* composition in an effective amount to an exercising subject.

It is to be appreciated that the term '*capsicum* composition' can be interpreted to be within the scope of the compositions which are comprised of *capsicum* extract or the extract formulated in a solid dosage form using food grade or pharmaceutically acceptable excipients. The compositions are comprised of compounds such as capsaicinoids and may be further also comprised of non-capsaicinoids. Capsaicinoids may be selected from the group of, but not limited to, the compounds such as capsaicin, dihydrocapsaicin, nordihydrocapsaicin, homocapsaicin, dihydrohomocapsaicin, 6",7"-dihydro-5',5'"-dicapsaicin, 5,5'-dicapsaicin, and mixtures thereof. Non-capsaicinoid compounds may be selected from flavonoids and saponins, and mixtures thereof. *Capsicum* compositions herein include capsaicinoids and can be used in the form of an extract or formulated as an extended and sustained release stable, free flowing, solid composition suitable for formulating into tablets, capsules, blended powders, licaps, ointments, pastes, lotions, liniments, mouthwashes, gargles, consumable dry syrups, liquid syrups, health drinks, diet drinks, fruit juices, soft drinks and the like. A *capsicum* composition herein may be prepared by solvent extraction to get *capsicum* extract comprising of capsaicinoids. The *capsicum* extract may be administered or may be formulated in the form of a solid dosage form, convenient to administer to exercising subjects as per methods described herein. The formulation may be prepared as extended and sustained release beadlets or spray dried powder using the methods known to person skilled in the art.

It is to be appreciated that the term 'effective amount' can be interpreted to be within the scope of amount of capsaicinoids comprised in *capsicum* composition, which is administered to exercising subjects, such that it is useful to bring out the desired effect and also avoids any adverse effect, over the time duration which is recommended for administration of the composition to the subjects. As per the methods described herein, the dose is delivered in the range of at or about 0.01 mg/kg body weight to at or about 200 mg/kg body weight of capsaicinoids, or at or about 10 mg/kg body weight/day to at or about 100 mg/kg body weight/day of capsaicinoids to a subject undergoing physical indoor and/or outdoor activities. The effective amount may vary depending upon the age and body weight of the subject or depending upon the type of activity the subject is undergoing such as sports. In such cases *capsicum* compositions may be administered with one or more other nutrients such as proteins, essential amino acids, or muscle stimulants, which may effectively lower the daily dose of the *capsicum* composition.

In an embodiment, a method for improving physical performance and endurance includes administering a *capsicum* composition in an effective daily dose including an amount of capsaicinoids, to a subject undergoing indoor or outdoor physical activities.

It is also to be appreciated that the term 'exercising subject or the subject undergoing physical activity' as used herein can be interpreted to mean that it is the practical or experimental condition for evaluating effect of *capsicum* composition in terms of exercise performance and endurance, wherein the composition is administered to the subjects who are undergoing exercise at the time of evaluation. It is also the condition which is advised as per the methods described herein, to achieve the intended result from administration of *capsicum* compositions in effective dose. In an embodiment, subjects, who are administered the *capsicum* composition are also subjected to specific type and duration of exercise. The effect of *capsicum* composition and exercise in combination is evaluated according to the method described herein. The term can be also interpreted as the recommended condition for the subjects who are administered with *capsicum* composition, so that the desired effect is obtained. In an embodiment, the subjects who are doing physical indoor and/or outdoor activities such as sports, exercise, or strenuous other activities benefit more due to administration of *capsicum* compositions of the invention.

Such benefits of *capsicum* composition administration are observed in exercising subjects as compared to those who are administered the composition but not doing any physical activity or exercise, and as compared to subjects who are exercising but not administered with *capsicum* composition.

In an embodiment, the level of activity as shown for example in the in-vivo study, can include treadmill running for a specific time interval, e.g. about 15 to 20 minutes, can be called a minimum duration of exercise activity such as in an animal model. In an embodiment, walking for a human can include about 30 minutes, and can be considered as a minimum duration of exercise activity, and where such intensity can vary from person to person.

The performance duration, endurance and stamina of such physically active subjects is enhanced because of administration of an effective amount of *capsicum* composition including capsaicinoids. However compositions described herein can be also administered to a subject at rest and can be asked to have their daily activities to get desired benefit or to increase stamina required for some physical strenuous activities. In its still wider meaning, the term 'exercising subject' also means that the subject is carrying out some type of physical indoor and/or indoor activity such as sports, exercise and other strenuous activities selected from the group of, but not limited to aerobic exercises, anaerobic exercises, fitness exercises, trekking, jogging, staircase climbing, jumping, walking and the like or the combinations thereof.

*Capsicum* compositions as described herein may be administered alone or in combination with one or more other nutrients, health supplements, muscle enhancers, stimulants, essential amino acids and/or anabolic ingredients for improving the performance and endurance during indoor and/or outdoor activities such as for example exercise, sports or other activities.

*Capsicum* compositions herein are obtained from natural resources by human intervention and are safe for administration.

In an embodiment, a method for improving exercise performance and endurance includes administering an effective amount of capsaicinoids from a *capsicum* composition to an exercising subject. According to the method, when *capsicum* composition is administered to deliver an effective amount of capsaicinoids to a subject undergoing indoor or outdoor physical activity, such as for example exercise or sports, improvement in performance as well as endurance are observed. The method results in improvement in fatigue suppression during endurance exercise and post-exercise recovery from muscle fatigue and/or muscle soreness.

In an embodiment, the composition as described herein may be comprised of *capsicum* extract alone or *capsicum* extract formulated as an extended and sustained release stable, free flowing, solid composition including, in some embodiments, capsaicinoids and/or derivatives, and employing at least one or more food grade excipients.

By "derivatives" it is meant as compounds derived or obtained from parent compounds by replacement of one atom with another atom or group of atoms. For example, derivatives of capsaicinoids can be nor-capsaicinoids.

In an embodiment, a *capsicum* composition includes a *capsicum* extract prepared for example from various varieties of paprika. In an embodiment, a *capsicum* composition includes chemical constituents including capsaicinoids and one or more other compounds such as non-capsaicinoids.

In an embodiment, a *capsicum* extract is prepared from various varieties of paprika selected from the group of, but not limited to, varieties such as for example Teja and Namdhari. In an embodiment, the composition herein includes a *capsicum* extract obtained from varieties of *Capsicum annum* such as Teja and Namdhari. In an embodiment, an industrially viable process is provided for preparation of a *capsicum* composition by employing non-polar, semi-polar, polar solvents or combinations thereof in suitable ratios. In an embodiment, a *capsicum* composition is prepared using a combination of polar and non-polar solvents in a suitable ratio for an extraction cycle, followed by purification of the extract by using polar solvent(s) to obtain the extract. The composition is safe for human consumption. In an embodiment, the composition includes a biologically active chemical constituent including capsaicinoids and in some embodiments, further includes one or more other compounds such as non-capsaicinoids.

The methods described herein include administering an effective amount of a *capsicum* composition in the form of a *capsicum* extract or in the form of the extract formulated using at least one pharmaceutically and/or nutraceutically acceptable excipient to obtain a stable dosage form, convenient for administration. The excipient may be selected from the group of, but not limited to a carrier, antioxidant, stabilizer, diluent, coating polymer, solvent alone, or a mixture thereof. *Capsicum* compositions as described herein are comprised of compounds, including capsaicinoids or capsaicinoids and/or non-capsaicinoids. The capsaicinoid compound(s) present in the *capsicum* composition may be selected from, but not limited to, the compounds such as capsaicin, dihydrocapsaicin, nordihydrocapsaicin, homocapsaicin, dihydrohomocapsaicin, 6",7"-dihydro-5',5"'-dicapsaicin, 5,5'-dicapsaicin, and mixtures thereof.

In an embodiment, a *capsicum* composition as described herein is comprised of either *capsicum* extract alone containing pungent and oily capsaicinoids or the extract is formulated using at least one food grade excipient to entrap the extract at high shear pressure. Due to the high shear pressure extract containing capsaicinoids is entrapped in a carrier which delays or extends the release of the active ingredient thus reducing the pungency and irritation characteristic of the active ingredient, which would otherwise release in gastric region. The pungency can be further reduced or masked by coating the polymer entrapped substance with an excipient such as a polymer that can form an effective barrier between pungent active and the outside environment and thus further sustains the release of the active substance and makes the present formulation palatable and safe for human consumption.

In an embodiment, an extended and sustained release *capsicum* composition herein includes a spheroidal nutrient core containing the active substance and at least one more excipient; and a protective polymeric enteric coat; wherein the coating facilitates gradual and uniform release of high dosage of the active substance to reduce irritation and minimize abdominal pain and gastric discomfort associated with its release.

In an embodiment, the oily and pungent capsaicinoid used in the *capsicum* composition is selected from a group consisting of *capsicum* extract; *capsicum* oleoresin; capsaicin crystals. It may be used either alone or is present in the range of at or about 0.1 to at or about 90% of the total weight of *capsicum* composition, formulated using at least one food grade excipient.

In an embodiment, the oily and pungent capsaicinoid used in the *capsicum* composition is present in the range of at or about 0.1 to at or about 40% w/w of the *capsicum* composition.

In an embodiment, the oily and pungent capsaicinoid used in the *capsicum* composition is present in the range of at or about 0.1 to at or about 20% w/w of the *capsicum* composition.

In an embodiment, the oily and pungent capsaicinoid used in the *capsicum* composition is present in the range of at or about 0.1 to at or about 2% w/w of the *capsicum* composition.

In an embodiment, the oily and pungent capsaicinoid used in the *capsicum* composition is present in the range of at or about 0.1 to at or about 1% w/w of the *capsicum* composition.

In an embodiment, the oily and pungent capsaicinoid used in the *capsicum* composition is present in the range of at or about 1 to at or about 90% w/w of the *capsicum* composition.

In an embodiment, the oily and pungent capsaicinoid used in the *capsicum* composition is present in the range of at or about 1 to at or about 40% w/w of the *capsicum* composition.

In an embodiment, the oily and pungent capsaicinoid used in the *capsicum* composition is present in the range of at or about 1 to at or about 20% w/w of the *capsicum* composition.

In an embodiment, the oily and pungent capsaicinoid used in the *capsicum* composition is present in the range of at or about 1 to at or about 2% w/w of the *capsicum* composition.

In an embodiment, the oily and pungent capsaicinoid used in the *capsicum* composition is present in the range of at or about 2 to at or about 90% w/w of the *capsicum* composition.

In an embodiment, the oily and pungent capsaicinoid used in the *capsicum* composition is present in the range of at or about 2 to at or about 40% w/w of the *capsicum* composition.

In an embodiment, the oily and pungent capsaicinoid used in the *capsicum* composition is present in the range of at or about 2 to at or about 20% w/w of the *capsicum* composition.

In an embodiment, the oily and pungent capsaicinoid used in the *capsicum* composition is present in the range of at or about 20 to at or about 90% w/w of the *capsicum* composition.

In an embodiment, the oily and pungent capsaicinoid used in the *capsicum* composition is present in the range of at or about 20 to at or about 40% w/w of the *capsicum* composition.

In an embodiment, the oily and pungent capsaicinoid used in the *capsicum* composition is present in the range of at or about 40 to at or about 90% w/w of the *capsicum* composition.

In an embodiment, the excipient can be a carrier selected from microcrystalline cellulose, Avicel® PH 101, Avicel® PH 102, Avicel® PH 103, Avicel® PH 105, Avicel® PH 112, Avicel® PH 113, Avicel® PH300, Avicel® PH212, Avicel® PH 301, Avicel® PH 302, colloidal grades Carboxymethyl cellulose Sodium and other cellulose containing polymers and their derivatives or mixtures thereof.

In an embodiment, the excipient is a sugar selected from the derivatives of sugar such as Mannitol, sucrose, xylitol, sorbitol, Maltitol, Lactitol, Isomalt or mixtures thereof.

In an embodiment, a surfactant is selected from polysorbate, sodium lauryl sulfate, sorbitanmonooleate, and other surfactants of the same class or mixtures thereof. It is appreciated that in an embodiment, a surfactant is an acceptable excipient for the compositions herein.

In an embodiment, a polymer is used for preventive coating and/or binders and may be are elected from Methyl Cellulose, Agar, Sodium Alginate, Hydroxy Propyl Methyl Cellulose, Hydroxy Propyl Cellulose, Microcrystalline Cellulose, Polyvinyl Pyrrolidone, Starch, Gum Arabic, Xanthan Gum, Polyethylene Glycols, preferably, Microcrystalline Cellulose, Hydroxy Propyl Cellulose, Methyl Cellulose, Hydroxy Propyl Methyl Cellulose, etc., more preferably, Hydroxy Propyl Methyl Cellulose, Methacrylates, Phthalate methyl acrylate-methacrylic acid copolymers, cellulose acetate succinate, polyvinyl acetate phthalate, Marcoat containing polymers and there derivatives or mixtures thereof.

In an embodiment, the solvent employed may be selected from acetone, hexane, ethyl acetate, Isopropyl alcohol, ethanol, dichloromethane, methanol and the like or the combination thereof. In an embodiment, the solvent may be selected from acetone, ethanol, dichloromethane, Isopropyl alcohol. In an embodiment, the solvent may be selected from Dichloromethane and Isopropyl alcohol.

In an embodiment, a free flowing, stable and solid *capsicum* composition as described herein is prepared by extrusion spheronization or by spray drying method.

In an embodiment, the effect of *capsicum* composition is evaluated by administering an effective amount of capsaicinoids to an exercising subject, for improving exercise performance and endurance.

In an embodiment, a *capsicum* composition herein may be administered to a subject in the form of an extract or as a solid oral dosage formulation, so as to provide daily dose of at least 0.01 mg/kg body weight to at or about 200 mg/kg body weight of capsaicinoids, or at a daily dose of at or about 10 mg/kg body weight to at or about 100 mg/kg body weight of capsaicinoids.

In an embodiment, a method includes evaluating the effect of *capsicum* composition through an in-vitro cell-line study to understand the effect on sports nutrition biomarkers, mitochondrial oxygen consumption, mitochondrial mass, IGF (Insulin like growth factor) and cortisol release. In an embodiment, a *capsicum* extract may be used in such in-vitro study and the effects monitored.

Mitochondria represent the principal energy source in cells, converting nutrients to energy via cellular respiration. The function and content of mitochondria increase with physical training and decrease with physical inactivity. An alteration in the rate of oxygen consumption can serve as a useful indicator of mitochondrial dysfunction. By measuring oxygen consumption, a direct and specific assessment of the functioning of the electron transport chain (the key element of oxidative phosphorylation and cellular metabolism) may be obtained. Mitochondrial abundance (mass) can also be used as an indicator of mitochondrial biogenesis.

As a direct result of aerobic exercise, elevated oxygen consumption contributes to an increase in the circulation of glucocorticoids, such as cortisol. During exercise training, cortisol causes rapid mobilization of fat, protein, and carbohydrates, providing the body with resources to manage an imbalance in homeostasis. However, cortisol is catabolic, decreasing muscle growth hormones, such as insulin-like growth factor (IGF)-1. Conversely, is anabolic, promoting protein synthesis and is thus considered as important biomarker for fitness and exercise training.

In an embodiment, methods described herein including evaluating the effect of a *capsicum* composition through an in-vivo study in animal models and human volunteers through plasma, muscle protein analysis and checking effect on physical performance, endurance, exhaustion time and actual run time. In an embodiment, a *capsicum* composition in the form of a *capsicum* extract or beadlets may be administered in such study.

In an embodiment, compositions as described herein are studied in experimental animal models to investigate the effect of administration on changes in serum parameters, antioxidant status of muscles in rats after exhaustive exercise. The effects can also be investigated on exercise performance, exercise time of exhaustion and changes in cardio-metabolic health markers such as HO-1 and silent mating type information regulation 2 homolog) 1 (SIRT1) pathways in the skeletal muscles of exercise-trained and sedentary rats.

The methods as described herein promote exercise performance and endurance through effective utilization of lipids such as cholesterol and triglycerides. The method as described herein also increases phosphorylated AMP activated protein kinase (pAMPK) and Nuclear erythroid derived factor-like 2 (Nrf2), thus reducing inflammatory process and improving exercise performance. The method also reduces lactate amount in muscles, enhances running performance, increases heme-oxygenase (HO-1) and decreases interleukin (IL-10) and thus enhances exhaustion time as well as running performance in exercising subject.

Exercise results in increased oxidative stress and capsaicinoids from *capsicum* compositions help to reduce oxidative stress and enhance antioxidant and anti-inflammatory effects. Activation of AMPK promotes glucose uptake, fatty acid oxidation, mitochondrial biogenesis, and insulin sensitivity, AMPK is activated by low energy status (increased AMP/ADP: ATP) such as during exercise, and regulates metabolic process and energy homeostasis by switching off ATP consuming pathways (fatty acid and cholesterol synthesis) and switching on ATP generating processes (glucose uptake and fatty acid oxidation).

In an embodiment, methods described herein lower cholesterol and triglyceride levels and exhibit increased antioxidant capacity. In an embodiment, a method for enhancing exercise endurance and exhaustion time includes administering an effective amount of a *capsicum* composition to an exercising subject, which enhances an antioxidant amount in the subject's body and decreases lactates, thus resulting in recovery from muscle fatigue during exercise and/or post exercise.

In an embodiment, a method described herein includes administering an effective amount of capsaicinoids of a *capsicum* composition to a subject who is undergoing physical activity, wherein it also lowers oxidative stress. *Capsicum* compositions as described herein are stable and safe for oral administration and are prepared using conventional equipment.

The Examples below are provided to illustrate examples of the compositions and methods described herein.

EXAMPLES

Example 1: In-Vitro Cell Line Study for Effect of *Capsicum* Compositions on Sports Nutrition Biomarkers Preparation of C2C12 Cell Line C2C12 cells (ATCC® CRL-1772) were seeded in 24- or 96-well culture plates as undifferentiated myoblasts and grown to 100% confluency in ATCC-formulated Dulbecco's Modified Eagle's Medium (DMEM) supplemented with 10% heat-inactivated fetal bovine serum (FBS). Upon reaching confluency, cells were induced to differentiate from myoblasts into multinucleated, fused myotubes, which exhibit similar characteristics to mature muscle cells.

Cell culture conditions were maintained at 37° C. in a humidified atmosphere of 5% $CO_2$/95% air. After 5 days of differentiation, cells were ready for incubation with *capsicum* composition as test inputs and without the composition as controls.

The effect of *Capsicum* composition (also abbreviated as Cap or capsimax in graphs and figures) was assessed using the following assays:

Cell Viability Measurement:

In order to determine appropriate dosages of capsaicinoids from *capsicum* composition for endurance/stamina related assays, differentiated C2C12 myotubes were treated with a range of capsaicinoids concentrations. Cell viability was assessed by MTT (3-(4, 5-desethyithiazol-2-yl)-2, 5-diphenyl-tetrazolium bromide) assay, a common measurement of the in vitro cytotoxicity of *capsicum* composition (called as test inputs in this study). Conversion of MTT reagent (yellow colour) to formazan (purple colour) by living cells provides an indication of mitochondrial activity, which is directly related to cell viability. C2C12 cells were seeded in 96-well culture plates at a density of $2 \times 10^4$ cells/mL and induced to differentiate. After a 24-hour pre-treatment with a range of select test input concentrations, used medium was removed, replaced with MTT labeling reagent (5 mg/mL in phosphate buffered saline), and incubated for 4 hours. The purple coloured formazan crystals formed in the intact cells were then dissolved overnight with MTT solubilisation solution (10% SDS in 0.01 M HCl). After solubilisation of the formazan crystals, absorbance was measured at 570 nm with a microplate reader. Data obtained from this cytotoxicity testing allowed for dose range optimization of *capsicum* composition for further testing.

A. Effect of *Capsicum* Composition on Mitochondrial Oxygen Consumption

Extracellular oxygen consumption in differentiated C2C12 cells was measured by assessing phosphorescence of a porphyrin-based, water soluble, oxygen sensitive probe (MitoXpress®-Xtra-HS, Luxcel Biosciences). Probe fluorescence is quenched by molecular oxygen ($O_2$), resulting in lower probe signal. As cellular respiration reduces the concentration of $O_2$, probe signal increases. The rate of this increase is related to the rate of cellular oxygen consumption. C2C12 cells were seeded in 96-well culture plates at a density of $2 \times 10^4$ cells/mL, induced to differentiate, and incubated with MitoXpress probe (1 µM), in the presence or absence of select test inputs. High sensitivity mineral oil was added (100 µL/well) to increase assay sensitivity by minimizing interference from ambient $O_2$. Probe fluorescence was measured (excitation 380 nm, emission 645 nm) using a fluorescence plate reader.

B. Effect of *Capsicum* Composition on Mitochondrial Mass

The effect of treatment with *capsicum* compositions on mitochondrial mass was assessed by measuring changes in fluorescent intensity in differentiated C2C12 cells. The nonyl acridine orange (NAO) probe binds to cardiolipin in mitochondria, regardless of their energetic state, providing a measure of mitochondrial mass and an indication of mitochondrial biogenesis. C2C12 cells were seeded in 96-well culture plates at a density of $2 \times 10^4$ cells/mL, induced to differentiate, and pre-treated with *capsicum* composition or used as controls. Following treatment, media was replaced with NAO probe (100 ng/mL) and incubated for 30 mins at 37° C. in a humidified atmosphere of 5% $CO_2$/95% air. Probe fluorescence was measured (excitation 380 nm, emission 645 nm) using a fluorescence plate reader. Fluorescent intensity relative to untreated control was then calculated. To standardize probe fluorescence to protein content of the cells, total protein content (in µg) was assessed by bicinchoninic acid (BCA) using bovine serum albumin as standard.

C. Effect of *Capsicum* Composition on Insulin-Like Growth Factor-1 (IGF-1)

To evaluate the effect of *capsicum* composition treatment on IGF-1 concentrations in differentiated C2C12 cells, the mouse IGF-1 enzyme-linked immunosorbent assay (ELISA) kit (Sigma) was utilized. The kit provides a quantitative measurement of mouse IGF-1 in cell culture supernatants by employing an antibody specific coated 96-well plate. Standards and test samples were added to the coated plate and any IGF-1 present in the sample gets bound to the immobilized antibody. After washing away any unbound antibody, HRP-conjugated streptavidin was added to the wells. The wells were washed again, followed by addition of a colorimetric reagent. Colour was developed in proportion to the amount of bound IGF-1. The colour intensity was read at wavelength 450 with a microplate reader. Blank-corrected unknown sample protein concentrations were then extrapolated from a known standard curve.

D. Effect of *Capsicum* Composition on Cortisol Release in H295R Cell Line

H295R cells (ATCC® CRL-2128) were seeded in 24-well culture plates and grown to confluence in ATCC-formulated Dulbecco's Modified Eagle's Medium (DMEM). Cell culture conditions were maintained at 37° C. in a humidified atmosphere of 5% $CO_2$/95% air. Cells were incubated in the presence or absence of a *capsicum* composition and controls.

To evaluate the effect of *capsicum* composition on cortisol concentrations in H295R cells, the DetectX® (Arbor Assays) immunoassay was utilized. A cortisol standard was provided to generate a standard curve for the assay and all samples were read off the standard curve. Standards or samples (*capsicum* composition) were pipetted into a clear microtiter plate coated with an antibody. A cortisol-peroxidase conjugate was added to the standards and samples in the wells. The binding reaction was initiated by the addition of a monoclonal antibody to cortisol in each well. After one hour incubation, the plate was washed and substrate was added. The substrate was reacted with the bound cortisol-peroxidase conjugate. After a short incubation, the reaction was stopped and the intensity of the generated color was detected in a microtiter plate reader capable of measuring 450 nm wavelength. The concentration of cortisol in the samples was then calculated by extrapolating from the standard curve.

Results:

A. Evaluation of Mitochondrial Respiration (Oxygen Consumption) as Sports Nutrition Biomarker

TABLE 1

| Effect of capsicum composition on mitochondrial respiration | | | | | | | | |
|---|---|---|---|---|---|---|---|---|
| Mitochondrial respiration | Concentration | Fluorescent Intensity | | | | | | Relative to |
| Product | (ug/mL) | n = 1 | n = 2 | n = 3 | AVG | SD | SEM | control |
| control | N/A | 28.8 | 30 | 29.9 | 29.6 | 0.6 | 0.4 | 99.9 |
| Capsicum composition | 10 | 38.5 | 38.5 | 38.5 | 38.5 | 0 | 0.0 | 130.2 |

*Capsicum* compositions increased mitochondrial oxygen consumption (respiration) significantly as compared to control. The results of Tables 1 to 5 are of an in-vitro cell line study, where the composition is in the form of a *capsicum* extract not formulated using an excipient.

FIG. 1 shows the effect of *capsicum* composition on mitochondrial respiration.

TABLE 2

| Effect of Capsicum composition on mitochondrial mass in C2C12 cells | | | | | | | | |
|---|---|---|---|---|---|---|---|---|
| Mitochondrial Mass Product | Concentration (ug/mL) | Fluorescent Intensity | | | | | | Relative to control |
| | | n = 1 | n = 2 | n = 3 | AVG | SD | SEM | |
| control | N/A | 13673.0 | 13705.3 | 13769.3 | 13175.9 | 49.0 | 28.3 | 100 |
| Capsicum composition | 10 | 16271.7 | 16468.0 | 19181.7 | 17307.1 | 1626.4 | 939.0 | 126.2 |

Table 2 indicates that *capsicum* compositions enhanced mitochondrial mass in cell-line study as compared to control cells.

Figure 2:
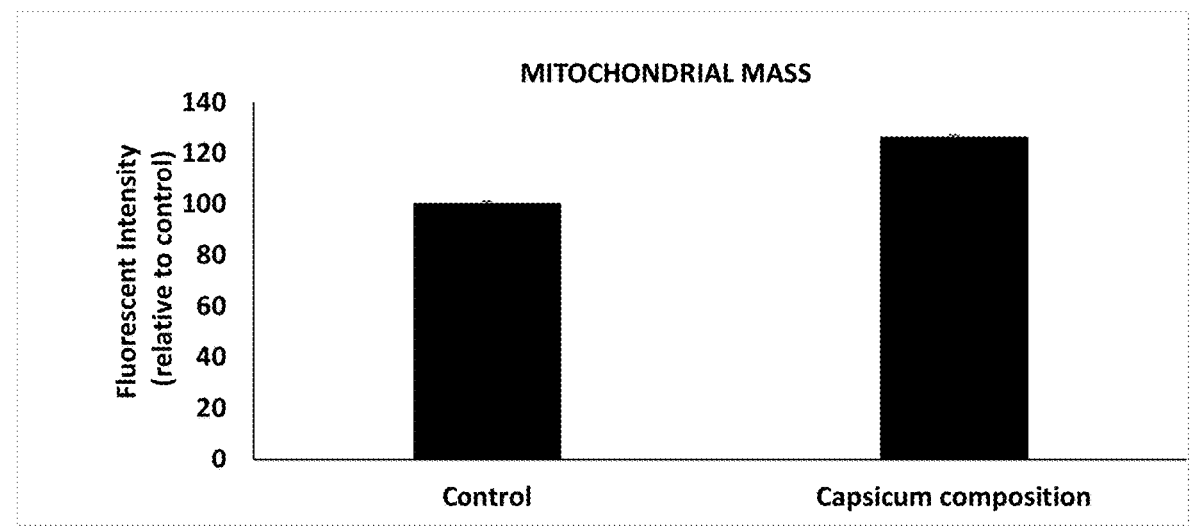
FIG. 2 shows the effect of *capsicum* composition on mitochondrial mass in cell-line study.

FIG. 2 shows the effects of *capsicum* composition on mitochondrial mass in cell-line study.

TABLE 3

| Effect of Capsicum composition on IGF-1 in cell-line study | | | | | | | | |
|---|---|---|---|---|---|---|---|---|
| IGF-1 Product | Concentration (ug/mL) | n = 1 Concentration (pg/ml) | n = 2 | n = 3 | AVG | SD | SEM | Relative to control |
| control | N/A | 36.3 | 34.7 | 31.9 | 34.3 | 2.22 | 1.28 | 100 |
| Capsicum composition | 10 | 42.5 | 43.2 | 36.2 | 40.6 | 3.82 | 2.20 | 118.5 |

Table 3 indicates that IGF-1 concentrations increased significantly when the cells were treated with *capsicum* compositions.

Figure 3:
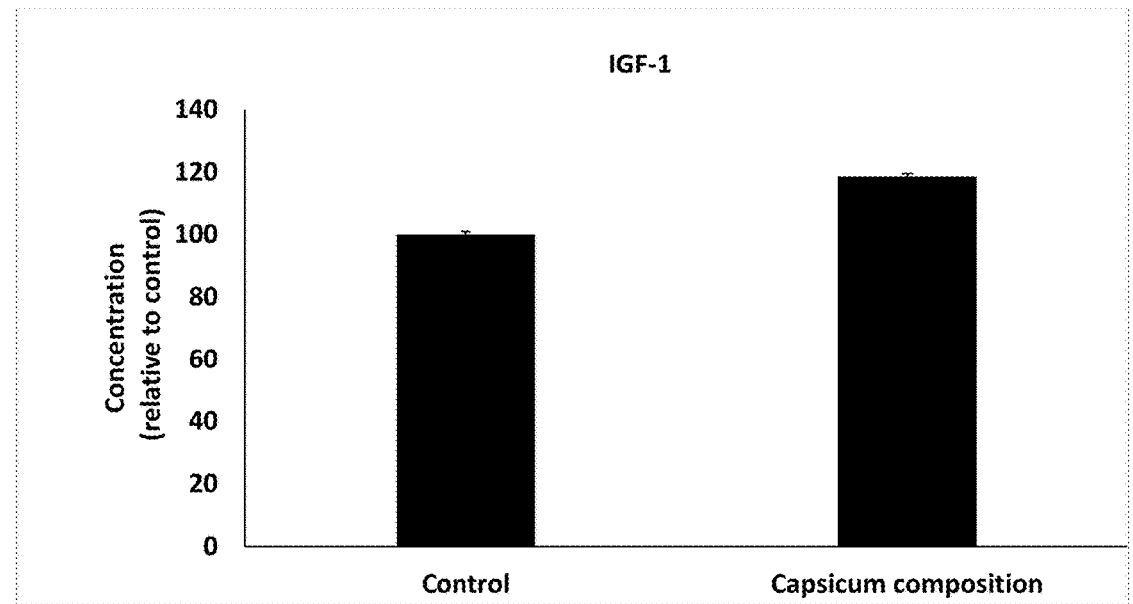
FIG. 3 shows the effect of *capsicum* composition on IGF-1 in cell-line study.

FIG. 3 shows the effect of *capsicum* composition on IGF-1 in cell-line study.

TABLE 4

| Effect of capsicum composition on cortisol release in cell-line study | | | | | | | | |
|---|---|---|---|---|---|---|---|---|
| Cortisol Product | Concentration (ug/mL) | n = 1 Concentration (pg/ml) | n = 2 | n = 3 | AVG | SD | SEM | Relative to control |
| control | N/A | 868.0 | 693.3 | 1200.9 | 920.7 | 257.9 | 148.9 | 100.0 |
| cAMP (negative control) | 1 mM | 1446.1 | 1042.2 | 2183.3 | 1557.2 | 578.6 | 334.1 | 169.1 |
| Capsicum composition | 10 | 1073.7 | 827.3 | 1659.8 | 1186.9 | 427.7 | 246.9 | 76.2 |

Capsicum compositions reduced cortisol release relative to control as indicated by cell-line study and thus enhance sport performance.

Figure 4:
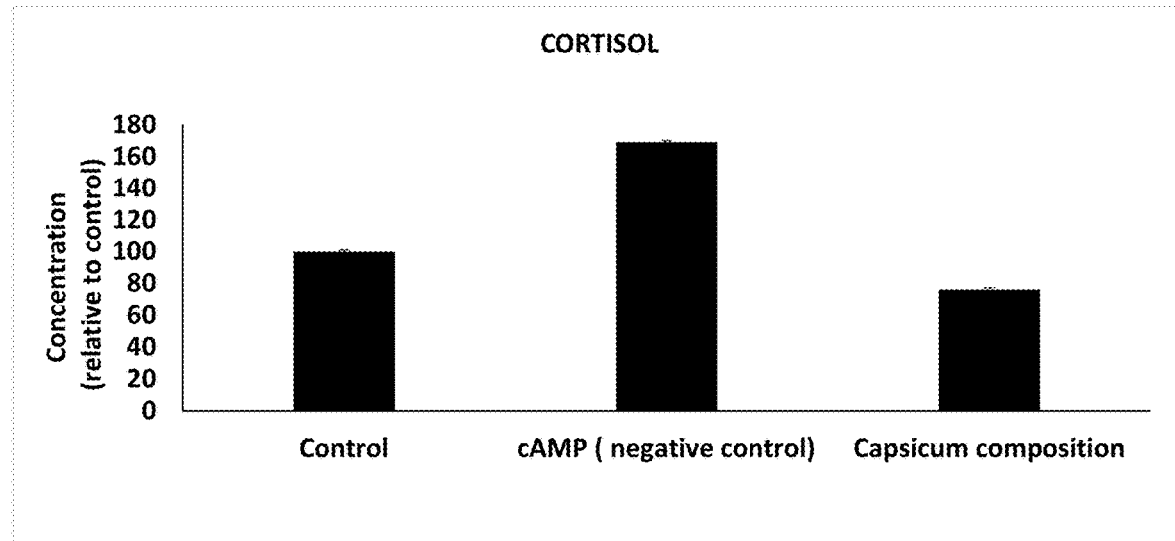
FIG. 4 shows the effect of *capsicum* composition on cortisol release as sports nutrition biomarker.

FIG. 4 shows the effect of capsicum composition on cortisol release as sports nutrition biomarker.

TABLE 5

Effect of capsicum composition on sports nutrition biomarkers in cell-line study

| Product | Mitochondrial Mass | Mitochondrial Respiration | IGF-1 | Cortisol |
|---|---|---|---|---|
| Control | 100 | 100.1 | 100 | 100 |
| cAMP(control) | | | | 169.1 |
| Capsicum composition | 126.2 | 130.2 | 118.5 | 76.2 |

Improvements in endurance and stamina are related to both the content and function of the mitochondrion. Mitochondrial mass can be used as an indicator of mitochondrial biogenesis. Similarly, oxygen consumption rate, a direct measurement of the functioning of the electron transport chain, is indicative of cellular metabolism. The cell-line study indicates that capsicum composition enhanced mitochondrial mass as well as mitochondrial oxygen consumption (respiration) significantly as compared to control.

Mitochondrial efficiency enhancement also results in increased glucocorticoids such as cortisol which is catabolic and can lead to decreases in protein synthesis and muscle growth hormones, such as IGF-1. In the sports nutrition market, controlling the deleterious catabolic effects of cortisol and enhancing the levels and activity of muscle building proteins such as IGF-1 is desired effect. Capsicum compositions showed good effect in all 4 assays related to endurance/stamina and thus represents a potentially beneficial natural supplement for this segment of the sports nutrition market.

Example 2: In-Vivo Study for Evaluation of Capsicum Composition

Animals and Exercise Protocol:

8-10 male Wistar rats per treatment arm (age: 8 week, weight: 180±20 g) were housed in a controlled environment and were provided with rat chow and water ad libitum. All experiments were conducted under the National Institutes of Health's Guidelines for the Care and Use of Laboratory Animals and approved by the Ethics Committee of the Veterinary Control Institute. Following a 7-day acclimatization period, rats of both the control and exercise groups were sub-divided into groups by matched body weight.

Animals were randomly divided into the following groups:

Group I - Control (No exercise or capsicum composition)
Group II-Control + capsicum composition(100 mg/kg body weight/day capsaicinoids)
Group III - only Exercise(No capsicum composition)
Group IV: Exercise + capsicum composition 100 mg/kg body weight/day capsaicinoids)

Similar to Example 1, the capsicum composition in this experiment is administered to animals in the form of the extract alone, so the dose is 100 mg/kg body weight/day of capsicum extract composition containing capsaicinoids.

Capsicum compositions were administered to group II and IV animals daily as an oral supplement for 8 weeks to deliver specific dose of capsaicinoids.

The exercise protocols were performed on a motor-driven rodent treadmill equipped with an electric shock grid on the rear barrier to provide exercise motivation to the animals. All exercise tests were performed during the same time period of the day to minimize diurnal effects. The animals in the chronic exercise groups were habituated by treadmill exercise over a 5-d period such as: 1st day 10 m/min, 10 min; 2nd day 20 m/min; 10 min, 3rd day 25 m/min, 10 min; 4th day 25 m/min, 20 min, and 5th day 25 m/min, 30 min. Thereafter, the animals were exercised at 25 m/min, 45 min/d, 5 d per week for 8 weeks (Liu et al. 2000.) To minimise diurnal effects, all animals were exercised at the same time.

Sample Collection

The rats were killed 24 h after the last exercise in the chronic exercise group by cardiac puncture. To minimize diurnal effects, all animals were killed at the same hours. Plasma samples were stored at $-80°$ C. until the time of analysis. Muscle samples (100 mg) were collected and frozen at $-80°$ C. for further analyses.

Laboratory Analyses

Plasma was used for the determination of glucose, lipid profile, cortisol, serotonin, testosterone, creatine kinase activity (CK), aspartate transaminase (AST), alanine transaminase (ALT), lactate dehydrogenase (LDH) activity, urea, creatinine) with an automatic analyser (Olympus). The serum and muscle malondialdehyde (MDA) levels were measured by HPLC (Shimadzu). The total superoxide dismutase (SOD), catalase (CAT) and glutathione peroxidase (GPx) were measured using a commercially available assay kit (Cayman Chemical, Ann Arbor, Mich., USA) according to the manufacturer's instructions. Inflammatory cytokines (TNFα, IL6 and IL10), C-reactive protein (CRP) were analyzed by ELISA. All proteins (AMP-activated protein kinase, SIRT1, mitochondrial transcription factor A, NF-κB, I-κB, Nrf2, HO-1) for pathways were analyzed by Western blot methods in muscle samples.

Histological Analysis

Samples of skeletal muscle (vastus lateralis) were collected from each rat in each experimental condition and fixed with a solution of 2% glutaraldehyde in phosphate buffer at $4°$ C. for 2 h. Samples were then washed several times in phosphate buffer and post fixed with 1% OsO4 (Osmium tetroxide) in phosphate buffer for 1 h at room temperature. After being washed in phosphate buffer, samples were dehydrated in a graded series of ethanol and embedded in Epon 812 resin (Fluka, Sigma-Aldrich). From each sample, sections of 500 nm were obtained with ultra microtome and subsequently stained with a solution of 1% toluidine blue buffered with borate. They were finally observed under light microscopy, and images were recorded by software.

Statistical Analyses

Data are given as mean±SEM. Sample size were calculated based on a power of 85% and a p value of 0.05. Given that assumption, a sample size of seven per treatment was calculated. Data analysis was done between control vs exercise vs control+capsicum composition vs exercise+effect of capsicum composition. The data were analyzed using the procedure of SAS (SAS Institute: SAS User's Guide: Statistics). The treatments were compared between control vs exercise vs control+capsicum vs exercise+product capsicum using ANOVA and student's unpaired t test; $P<0.05$ was considered statistically significant.

Results:

TABLE 6

Effect of capsicum composition on distance run aveavage per day and run to exhaustion
↑ Distance run average per day and ↑ run to exhaustion with CAPs supplementation

| | Groups | | | | | |
|---|---|---|---|---|---|---|
| Item | Control | CAPs | Exercise | Exercise + CAPs | SEM | --P-- |
| Distance run average per day, m | — | — | 1037.14 | 1099.86 | 9.88 | 0.004 |
| Run to exhaustion, min | 77.31$^c$ | 80.49$^c$ | 169.34$^b$ | 201.11$^a$ | 3.28 | 0.0001 |

Data are means the standard error of the mean (SEM).
Different superscripts (a-d) Indicate group mean differences (p < 0.05).

*Capsicum* compositions when administered to exercising subjects increased distance run average per day and run to exhaustion as compared to the subjects not administered with *capsicum* composition. Table 6 shows the effect of *capsicum* composition on exercise duration and time to exhaustion.

TABLE 7

Effect of capsicum composition on lipid profile in exercising subjects

| | Groups | | | | | |
|---|---|---|---|---|---|---|
| Item | Control | CAPs | Exercise | Exercise + CAPs | SEM | --P-- |
| Glucose. mg/dL | 101.57 | 99.14 | 91.43 | 93.86 | 5.14 | 0.512 |
| T-C. mg/dL | 75.14$^a$ | 70.57$^b$ | 74.00$^a$ | 47.86$^c$ | 0.70 | 0.0001 |
| TG. mg/dL | 103.71$^a$ | 100.14$^{ab}$ | 84.29$^b$ | 60.57$^c$ | 3.62 | 0.0001 |

T-C: Total Cholesterol; TG: Triglycerides Data are means the standard error of the mean (SEM).
Different superscripts (a-d) indicate group mean differences (p < 0.05).

*Capsicum* compositions decreased total cholesterol and triglycerides, when administered to exercising subjects.

TABLE 8

Effect of capsicum composition on lactates and muscle antioxidant activity

| | Groups | | | | | |
|---|---|---|---|---|---|---|
| Item | Control | CAPs | Exercise | Exercise + CAPs | SEM | --P-- |
| Lactate mg/dL | 9.66$^a$ | 8.77$^b$ | 7.47$^c$ | 5.43$^d$ | 0.17 | 0.0001 |
| Muscle MDA (nmol/mg protein) | 78.84$^a$ | 60.50$^b$ | 74.16$^a$ | 44.79$^c$ | 2.07 | 0.0001 |
| Muscle SOD (U/mg protein) | 0.22$^d$ | 0.43$^b$ | 0.34$^c$ | 0.56$^a$ | 0.01 | 0.0001 |
| Muscle GPx (U/mg protein) | 143.29$^c$ | 172.57$^b$ | 155.71$^{bc}$ | 203.86$^a$ | 5.13 | 0.0001 |

MDA: Malondialdehyde; SOD: superoxide dismutase; GPx: Glutathione peroxidase.
Data are means the standard error of the mean (SEM).
Different superscripts (a-d) indicate group mean differences (p < 0.05).

When *Capsicum* compositions were administered to exercising subjects, this resulted in decreased muscle lactate and muscle malonaldehyde, which indicates decreased oxidative stress. On the other hand SOD and GPx values increased in exercising subjects with *capsicum* compositions (Group IV), which suggested increased muscle antioxidant activity.

Figure 5:
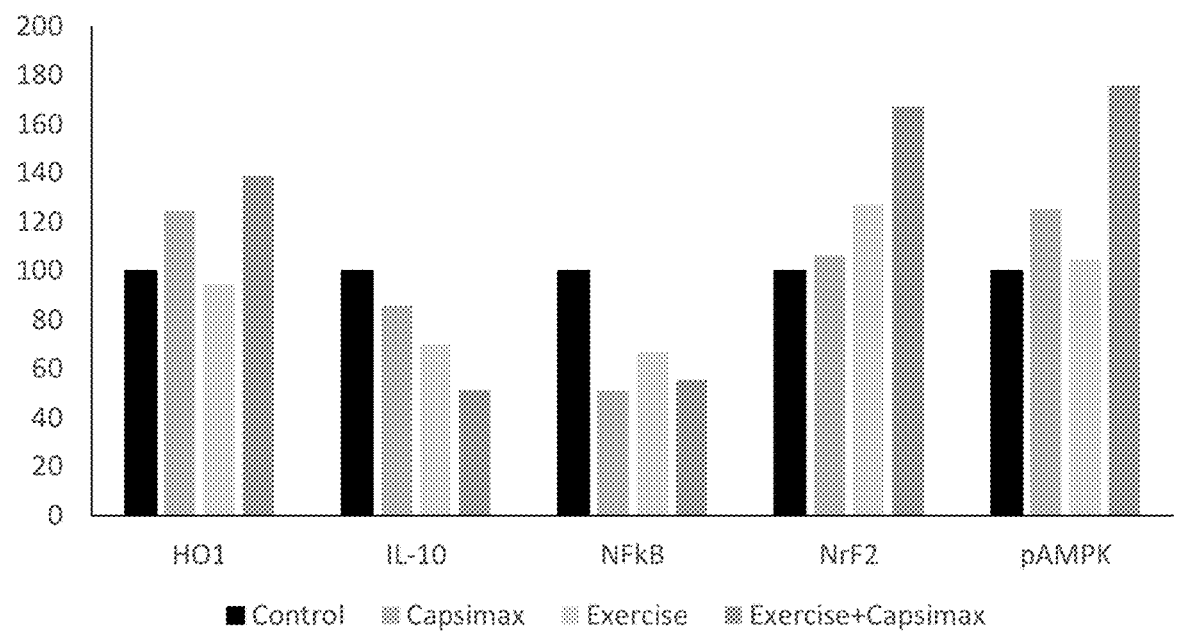
FIG. 5 shows an evaluation of the effect of *capsicum* composition in protein levels in all 4 groups.

FIG. 5 shows an evaluation of the effect of *capsicum* composition in protein levels in all 4 groups.

It was observed that oxidative stress marker such as NFkBand Interleukin-10 (IL-10) was decreased in group II and IV.

Protein levels of phosphorylated AMP-activated protein kinase (pAMPK), Nuclear factor (erythroid-derived 2)-like 2 (Nrf2), and heme oxygenase-1 (1101) were increased in Group IV. There were no significant differences in any of the end points in Group I and II.

The results suggested that dietary capsaicinoids enhance running performance and decreased oxidative stress. These results suggest that administration of *capsicum* compositions to the exercising subjects may enhance the effect of exercise by effective utilization of lipids by increasing pAMPK and Nrf2. Group IV significantly increased running performance and exhaustion time. In Group IV, significant decrease in triglycerides and cholesterol was observed compared with other treatments. A significant decrease in lactate, muscle oxidative stress and increase in muscle antioxidant activity were observed in Group IV. No significant changes in liver and kidney functions were observed in any of the treated groups.

Example 3: Human Umbilical Endothelial Cells Line Model to Study Nitric Oxide Effects by Capsicum Composition Human Umbilical Vein Endothelial Cells (HUVEC) were purchased from Clonetics (Cambrex, Inc., Walkersville, Md., USA) as a frozen stock (passage 3), defrosted and cultured in endothelial basal medium 2 growth media plus bullet kit (Cambrex, Inc.) containing 2% fetal calf serum, antibiotics and growth factor supplements at 37 C and 5% $CO_2$. The cells were passaged three times to provide a pool of cells to be used for experiments. Experiments were performed in six-well plates (Corning, Inc., Corning, N.Y., USA) when the cells were 80% confluent, at which stage the endothelial basal medium 2 growth media (2% fetal calf serum, with growth factors) was replaced with endothelial basal medium 2 control media (0.8% fetal calf serum, no growth factors) and incubated for 24 h (37C, 5% $CO_2$). Treatments were prepared in endothelial basal medium 2 containing 0.8% fetal calf serum and antibiotics but no other supplements. Capsicum composition was dissolved in water at three concentrations, as shown. Eighteen hours after treatment RNA was extracted. Real-time PCR was performed on selected list of genes using standard protocols.

| Name | CONC |
| --- | --- |
| Untreated (DMSO only) Control | 0 |
| Capsimax beadlets | 6.25 |
| Capsimax beadlets | 12.5 |
| Capsimax beadlets | 25 |
| Rosiglitazone | 10 |

Figure 6:
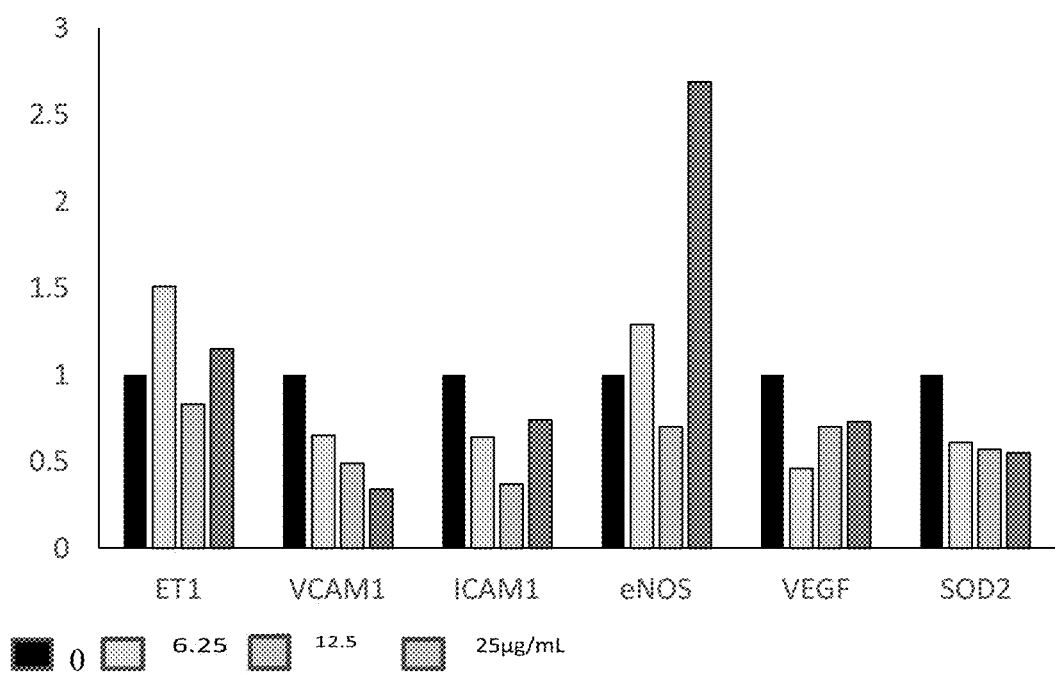
FIG. 6 shows the effect of *capsicum* composition on relative gene expression.

FIG. 6 shows the effect of capsicum composition on relative gene expression.

It was observed that capsicum compositions upregulated eNOSat higher concentration and down regulated ET1 in human umbilical endothelial cells. This indicates effect of exercise on decreasing reactive oxygen species, thus reducing oxidative stress in the system, as beneficial effect of administration of capsicum compositions in exercising subjects.

Example 4: Evaluation of Capsicum Composition as Sports Nutrition in Human Volunteers Capsicum formulation was administered to 152 normal to overweight females and males having BMI ranging from 18.3 to 30.0. Daily dosage of 2 mg capsaicinoids from 2% capsimax beadlets was administered for 7 days. Heart rate, general health status, and life style factors including exercise intensity were recorded at baseline and after 7 days. Effect of capsicum composition was evaluated and recorded in terms of duration of exercise and time to exhaustion at the end of 7 days.

At the end of 7 days it was observed that duration of exercise and time to exhaustion was significantly increased in individuals administered with capsicum composition. Subjects work out intensity also increased after capsicum supplementation.

The invention claimed is:

1. A method for improving physical performance, comprising:
administering, to a subject undergoing physical activity, a capsicum composition comprising a combination of capsaicinoids in an effective amount, the combination of capsaicinoids consisting of capsaicin, dihydrocapsaicin, and nordihydrocapsaicin, wherein the effective amount is a daily dose of about 0.01 mg/kg body weight to 1 mg/kg body weight of the combination of capsaicinoids, wherein the physical activity is treadmill exercise and wherein said amount of the combination of capsaicinoids is effective in decreasing levels of muscle lactates and muscle malondialdehyde (MDA) and increasing levels of superoxide dismutase (SOD) and glutathione peroxidase (GPx) in the subject as compared to a subject that has not been administered with the capsicum composition.

2. The method as claimed in claim 1, wherein the subject is a human being.

3. The method as claimed in claim 1, wherein the capsicum composition contains the combination of capsaicinoids formulated with at least one pharmaceutically and/or nutraceutically acceptable excipient selected from the group consisting of a sugar, a surfactant, and a polymer.

4. The method as claimed in claim 1, wherein the amount of the combination of capsaicinoids is effective in increasing levels of IGF-1 and decreasing release of cortisol in the subject as compared to a subject that has not been administered with the capsicum composition.

5. The method as claimed in claim 1, wherein the amount of the combination of capsaicinoids is effective in increasing levels of pAMPK (phosphorylated AMP-activated protein) and Nrf2 (Nuclear factor [erythroid-derived 2]-like 2) in the subject as compared to a subject that has not been administered with the capsicum composition.

6. The method as claimed in claim 1, wherein the subject has a BMI ranging from 18.3 to 30.0 and wherein the effective amount is about 2 mg of the combination of capsaicinoids.

* * * * *